(12) United States Patent
Fukudome et al.

(10) Patent No.: US 8,802,918 B2
(45) Date of Patent: Aug. 12, 2014

(54) WATER-ABSORBENT SHEET COMPOSITION

(75) Inventors: Shinya Fukudome, Himeji (JP); Junichi Maruo, Himeji (JP); Masayoshi Handa, Himeji (JP); Kiyoshi Yamaguchi, Himeji (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 454 days.

(21) Appl. No.: 13/142,527

(22) PCT Filed: Jun. 29, 2009

(86) PCT No.: PCT/JP2009/061814
§ 371 (c)(1),
(2), (4) Date: Jun. 28, 2011

(87) PCT Pub. No.: WO2010/076857
PCT Pub. Date: Jul. 8, 2010

(65) Prior Publication Data
US 2011/0270204 A1    Nov. 3, 2011

(30) Foreign Application Priority Data
Dec. 29, 2008 (JP) ................................. 2008-335706

(51) Int. Cl.
*A61F 13/15* (2006.01)
(52) U.S. Cl.
USPC ........... 604/367; 604/372; 604/368; 604/364; 604/378
(58) Field of Classification Search
USPC ................... 604/367, 372, 368, 364, 378
See application file for complete search history.

(56) References Cited

U.S. PATENT DOCUMENTS

| 5,562,646 A | 10/1996 | Goldman et al. |
| 5,599,335 A | 2/1997 | Goldman et al. |

(Continued)

FOREIGN PATENT DOCUMENTS

| CN | 1736355 A | 2/2006 |
| CN | 1976663 A | 6/2007 |

(Continued)

OTHER PUBLICATIONS

Chinese Office Action issued Apr. 15, 2013, in China Patent Application No. 200980153186.1.

(Continued)

*Primary Examiner* — Jacqueline F. Stephens
(74) *Attorney, Agent, or Firm* — Oblon, Spivak, McClelland, Maier & Neustadt, L.L.P.

(57) ABSTRACT

A water-absorbent sheet composition containing a structure in which an absorbent layer containing a water-absorbent resin and an adhesive is sandwiched with two or more sheets of hydrophilic nonwoven fabrics, wherein the water-absorbent sheet composition has a structure in which the absorbent layer is separated in divided parts of a primary absorbent layer and a secondary absorbent layer with a water-permeable substrate having a water permeability index of from 20 to 90, and wherein the water-absorbent resin is contained in the absorbent layer in an amount of from 100 to 1000 $g/m^2$. The water-absorbent sheet composition of the present invention exhibits some excellent effects that the water-absorbent sheet composition is capable of accomplishing thinning and avoidance of gel blocking phenomenon and liquid leakage, while obtaining basic properties as a water-absorbent sheet composition at a high level, even for a water-absorbent sheet composition containing a very small amount of pulps.

21 Claims, 4 Drawing Sheets

(56) References Cited

U.S. PATENT DOCUMENTS

| | | | |
|---|---|---|---|
| 5,669,894 A | 9/1997 | Goldman et al. | |
| 2002/0143309 A1* | 10/2002 | Glasgow et al. | 604/378 |
| 2005/0085604 A1* | 4/2005 | Handa et al. | 526/227 |
| 2006/0184149 A1 | 8/2006 | Kasai et al. | |
| 2008/0038504 A1 | 2/2008 | Manabe et al. | |
| 2008/0044616 A1 | 2/2008 | Hanao et al. | |
| 2008/0262459 A1 | 10/2008 | Kamoto et al. | |
| 2008/0312623 A1 | 12/2008 | Hundorf et al. | |
| 2008/0312627 A1 | 12/2008 | Takeuchi et al. | |
| 2009/0004435 A1 | 1/2009 | Hanao et al. | |
| 2009/0247977 A1 | 10/2009 | Takeuchi et al. | |
| 2011/0111199 A1 | 5/2011 | Takatori et al. | |
| 2011/0151228 A1 | 6/2011 | Takatori et al. | |

FOREIGN PATENT DOCUMENTS

| | | |
|---|---|---|
| JP | 64 3615 | 1/1989 |
| JP | 02 048944 | 2/1990 |
| JP | 6 059039 | 8/1994 |
| JP | 8 57311 | 3/1996 |
| JP | 9 510889 | 11/1997 |
| JP | A-H 10-118117 | 5/1998 |
| JP | 2000 238161 | 9/2000 |
| JP | 2002 113800 | 4/2002 |
| JP | 2002 224161 | 8/2002 |
| JP | 2003 11118 | 1/2003 |
| JP | A 2004-275225 | 10/2004 |
| WO | WO 2008/093660 | 8/2008 |

OTHER PUBLICATIONS

U.S. Appl. No. 13/695,515, filed Oct. 31, 2012, Fukudome, et al.
U.S. Appl. No. 13/819,591, filed Feb. 27, 2013, Matsushita, et al.
U.S. Appl. No. 13/521,491, filed Jul. 11, 2012, Fukudome, et al.
U.S. Appl. No. 13/521,572, filed Jul. 11, 2012, Matsushita, et al.
U.S. Appl. No. 13/521,464, filed Jul. 11, 2012, Hinayama, et al.
U.S. Appl. No. 13/521,376, filed Jul. 10, 2012, Yamaguchi, et al.
U.S. Appl. No. 13/637,153, filed Sep. 25, 2012, Takatori, et al.
Extended European Search Report issued Sep. 27, 2013, in European Patent Application No. 09836197.5.
U.S. Appl. No. 13/259,776, filed Sep. 23, 2011, Takatori, et al.
U.S. Appl. No. 13/500,550, filed Apr. 5, 2012, Maruo, et al.
International Search Report issued Oct. 6, 2009 in PCT/JP09/061814 filed Jun. 29, 2009.
U.S. Appl. No. 13/145,278, filed Jul. 19, 2011, Kakimoto, et al.
Japanese Office Action issued in Patent Application No. 2010-544861 mailed Mar. 12, 2014.

* cited by examiner

WATER-ABSORBENT SHEET COMPOSITION

TECHNICAL FIELD

The present invention relates to a thin water-absorbent sheet composition which can be used in the fields of hygienic materials and the like. More specifically, the present invention relates to a water-absorbent sheet composition containing a very small amount of pulp, which can be suitably used in absorbent articles, such as disposable diapers and incontinence pads, having high absorbent properties even when being thin. Furthermore, the present invention relates to an absorbent article obtainable from the water-absorbent sheet composition.

BACKGROUND ART

Body liquid absorbent articles represented by disposable diapers or the like have a structure in which an absorbent material for absorbing a liquid such as a body liquid is sandwiched with a flexible liquid-permeable surface sheet (top sheet) positioned on a side contacting a body and a liquid-impermeable backside sheet (back sheet) positioned on a side opposite to that contacting the body.

Conventionally, there have been increasing demands for thinning and light-weighing of absorbent articles, from the viewpoint of designing property and convenience upon carrying, and efficiency upon distribution. Further, in the recent years, there have been growing needs for so-called eco-friendly intentions, in which resources are effectively utilized so that use of natural materials that require a long time to grow such as trees is avoided as much as possible, from the viewpoint of environmental protection. Conventionally, a method for thinning that is generally carried out in absorbent articles is a method of reducing hydrophilic fibers such as disintegrated pulp of a wood material, which has a role of fixing a water-absorbent resin in an absorbent material, while increasing a water-absorbent resin.

An absorbent material in which a water-absorbent resin is used in a large amount with a lowered proportion of a hydrophilic fiber is preferred in thinning, from the viewpoint of reducing bulky hydrophilic fibers while retaining a liquid. However, when a liquid distribution or diffusion upon actually using in an absorbent article such as disposable diapers is considered, there is a disadvantage that if a large amount of the water-absorbent resin is formed into a soft gel-like state by absorption, a so-called "gel-blocking phenomenon" takes place, whereby liquid diffusibility is markedly lowered and a liquid permeation rate of the absorbent material is slowed down. This "gel-blocking phenomenon" is a phenomenon in which especially when an absorbent material in which water-absorbent resins are highly densified absorbs a liquid, a water-absorbent resin existing near a surface layer absorbs the liquid to even more densify soft gel that forms near the surface layer, so that a liquid permeation into an internal of an absorbent material is inhibited, thereby making the internal of the water-absorbent resin incapable of efficiently absorbing the liquid.

In view of the above, conventionally, as a means of inhibiting gel blocking phenomenon which takes place by reducing hydrophilic fibers while using a water-absorbent resin in a large amount, for example, proposals such as a method using an absorbent polymer having such properties as specified Saline Flow Conductivity and Performance under Pressure (see Patent Publication 1), a method using a water-absorbent resin prepared by heat-treating a specified water-absorbent resin precursor with a specified surface crosslinking agent (see Patent Publication 2), and the like have been made.

However, in these methods, the absorption properties as absorbent materials in which water-absorbent resins are used in large amounts are not satisfactory. In addition, there arise some problems that the water-absorbent resin is subjected to be mobile before use or during use because hydrophilic fibers that play a role of fixing the water-absorbent resin are reduced. The absorbent material in which the localization of the absorbent resin takes place is more likely to cause gel-blocking phenomenon.

Further, in an absorbent material of which hydrophilic fibers that contribute to retention of the form are reduced has a lowered strength as an absorbent material, deformation such as twist-bending or tear before or after the absorption of a liquid is likely to take place. In an absorbent material with deformation, liquid diffusibility has markedly lowered, so that abilities inherently owned by the absorbent material cannot be exhibited. In order to try to avoid such phenomena, a ratio of hydrophilic fibers and a water-absorbent resin would be limited, thereby posing limitations in the thinning of an absorbent article.

In view of the above, in recent years, as a next generation style absorbent material which is capable of increasing a content of a water-absorbent resin while using hydrophilic fibers in an absorbent material as little as possible, studies have been widely made on an absorbent laminate that substantially does not contain hydrophilic fibers in an absorbent layer, a water-absorbent sheet composition or the like. For example, a method using an absorbent laminate comprising two pieces of nonwoven fabrics, and a reticular layer comprising two, upper and lower layers of hot melt adhesives provided between the nonwoven fabrics, in which the nonwoven fabrics are bonded with the reticular layer (see Patent Publication 3), and the like.

However, in a case where hydrophilic fibers are hardly used, the gel blocking phenomenon as mentioned above are likely to take place. Even in a case where gel blocking phenomenon does not take place, a thing that would serve the role of conventional hydrophilic fibers by which a body fluid such as urea is temporarily subjected to water retention and diffusion of the liquid to an overall absorbent material is lacking, so that a liquid leakage is likely to occur in the absorbent laminate, without being able to sufficiently capture the liquid.

Further, when an adhesive is used for retaining the shape of an absorbent laminate, the surface of an absorbent resin is coated with an adhesive, so that absorbent properties are likely to be lowered. Alternatively, an upper side and a lower side of nonwoven fabrics are firmly adhered with an adhesive to confine an water-absorbent resin in a pouched form or the like, so that the absorption properties inherently owned by the water-absorbent resin are less likely to be exhibited.

When adhesive strength of an absorbent laminate is weakened in order to improve absorption properties, not only a large amount of the absorbent resin is detached upon handling the laminate, thereby making unfavorable economically, but also the laminate is exfoliated due to deficiency in strength, so that there are some possibilities of loss of commercial values. In other words, if adhesion is strengthened, gel blocking phenomenon or liquid leakage occurs, and if adhesion is weakened, the detachment of a water-absorbent resin and the breaking of the laminate take place, so that an absorbent laminate or a water-absorbent sheet composition having satisfactory properties is not obtained.

There is also a method of immobilizing a water-absorbent resin to a substrate without using an adhesive, which is, for example, a method of adhering water-absorbent polymer particles in the process of polymerization to a synthetic fibrous substrate to carry out polymerization on the fibrous substrate (see Patent Publication 4), a method of polymerizing a monomer aqueous composition containing acrylic acid and an acrylic acid salt as main components on a nonwoven fabric substrate by means of electron beam irradiation (see Patent Publication 5), and the like.

In these methods, while the synthetic fibrous substrate is penetrated into the polymer particles to be firmly adhered, there are some disadvantages that it is difficult to complete the polymerization reaction in the substrate, so that unreacted monomers and the like remain in the substrate in large amounts.

In addition, a laminate having a 5-layered structure in which homogeneity is improved and a water-absorbent resin is effectively utilized is disclosed (see Patent Publication 6). The laminate might be effective for a trace amount of liquid (test solution: 0.2 cc); however, not only a total amount of the water-absorbent resin used is small but also a water-absorbent resin in a layer near human body (first absorbent layer) is in a relatively small amount; therefore, when an amount of liquid such as urine or blood is large, the amount of re-wet becomes large, thereby having a disadvantage of increased unpleasant feel.

PRIOR ART PUBLICATIONS

Patent Publications

Patent Publication 1: Japanese Unexamined Patent Publication No. Hei-9-510889
Patent Publication 2: Japanese Patent Laid-Open No. Hei-8-57311
Patent Publication 3: Japanese Patent Laid-Open No. 2000-238161
Patent Publication 4: Japanese Patent Laid-Open No. 2003-11118
Patent Publication 5: Japanese Patent Laid-Open No. Hei-02-048944
Patent Publication 6: Japanese Utility Model Laid-Open No. Hei-6-059039

SUMMARY OF THE INVENTION

Problems to be Solved by the Invention

An object of the present invention is to provide a water-absorbent sheet composition which is capable of accomplishing thinning and avoidance of gel blocking phenomenon, irrespective of having a large content of a water-absorbent resin, while obtaining fundamental properties (high strength, fast liquid permeation rate, small amount of re-wet, and small liquid leakage) as a water-absorbent sheet composition at a high level, even for a water-absorbent sheet composition containing a very small amount of pulps.

Means to Solve the Problems

Specifically, the gist of the present invention relates to:
[1] a water-absorbent sheet composition comprising a structure in which an absorbent layer containing a water-absorbent resin and an adhesive is sandwiched with two or more sheets of hydrophilic nonwoven fabrics, wherein the water-absorbent sheet composition has a structure in which the absorbent layer is separated in divided parts of a primary absorbent layer and a secondary absorbent layer with a water-permeable substrate having a water permeability index of from 20 to 90, and wherein the water-absorbent resin is contained in the absorbent layer in an amount of from 100 to 1000 g/m$^2$;
[2] a water-absorbent sheet composition comprising a structure in which an absorbent layer containing a water-absorbent resin and an adhesive is sandwiched with two or more sheets of hydrophilic nonwoven fabrics, wherein the water-absorbent sheet composition has a structure in which the absorbent layer is separated in divided parts of a primary absorbent layer and a secondary absorbent layer with a water-permeable substrate having a water permeability index of from 20 to 90, and wherein the water-absorbent resin is contained in the absorbent layer in an amount of from 200 to 800 g/m$^2$; and
[3] an absorbent article comprising the water-absorbent sheet composition as defined in the above [1] or [2], sandwiched between a liquid-permeable sheet and a liquid-impermeable sheet.

Effects of the Invention

The water-absorbent sheet composition of the present invention exhibits some excellent effects that the water-absorbent sheet composition is capable of accomplishing thinning and avoidance of gel blocking phenomenon and liquid leakage, while obtaining basic properties as a water-absorbent sheet composition at a high level, even for a water-absorbent sheet composition containing a very small amount of pulps.

MODES FOR CARRYING OUT THE INVENTION

Figure 1:
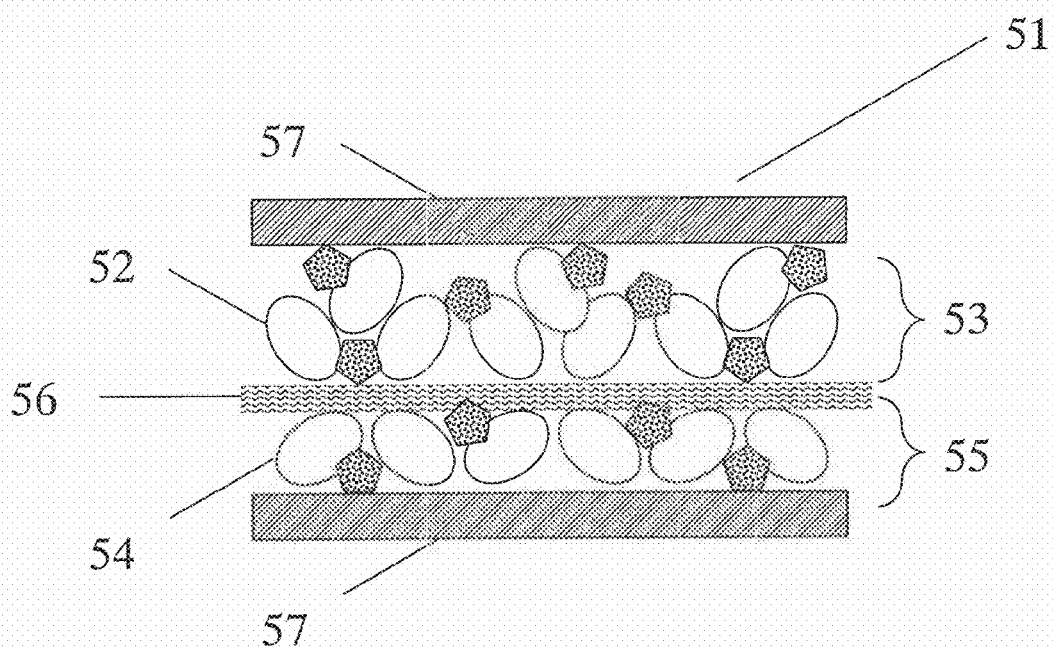
FIG. 1 is an enlarged cross-sectional view schematically showing one example of a structure of a water-absorbent sheet composition of the present invention.

The water-absorbent sheet composition of the present invention has a structure in which an absorbent layer containing a water-absorbent resin and an adhesive is sandwiched with two or more sheets of hydrophilic nonwoven fabrics, wherein the water-absorbent sheet composition has a structure in which the absorbent layer is separated in divided parts of a primary absorbent layer and a secondary absorbent layer with a water-permeable substrate having a specified range of a water permeability index, and further that the water-absorbent sheet composition of the present invention contains a water-absorbent resin in a specified range, so that the absorbent layers do not substantially contain hydrophilic fibers such as pulps that contribute to fixation of a water-absorbent resin in the absorbent layers, and shape retention of the absorbent layer, and whereby the water-absorbent sheet composition obtained is thin and has high-performance, with a very small amount of pulps used.

As the kinds of the water-absorbent resins, commercially available water-absorbent resins can be used. For example, the water absorbent resin includes hydrolysates of starchacrylonitrile graft copolymers, neutralized products of starch-acrylic acid graft polymers, saponified products of vinyl acetate-acrylic acid ester copolymers, partially neutralized products of polyacrylic acid, and the like. Among them, the partially neutralized products of polyacrylic acids are preferred, from the viewpoint of production amount, production costs, water absorbency of product, and the like. Methods for synthesizing partially neutralized products of polyacrylic acid include reversed phase suspension polymerization method and aqueous solution polymerization method. Among them, the water-absorbent resins obtained according to reversed phase suspension polymerization are more preferably used, from the viewpoint of excellent flowability of the resulting particles, smaller amounts of fine powder, high water-absorbent properties, such as water absorption capacity and water-absorption rate.

The partially neutralized product of a polyacrylic acid has a degree of neutralization of preferably 50% by mol or more, and even more preferably from 70 to 90% by mol, from the viewpoint of increasing osmotic pressure of the water-absorbent resin, thereby increasing water absorbency.

The water-absorbent resin is contained, in a total amount of a primary absorbent layer and a secondary absorbent layer, in the water-absorbent sheet composition of from 100 to 1000 g per one square meter of the water-absorbent sheet composition, i.e. 100 to 1000 g/m$^2$, preferably from 200 to 800 g per one square meter of the water-absorbent sheet composition, i.e. 200 to 800 g/m$^2$, more preferably from 220 to 700 g/m$^2$, even more preferably from 250 to 600 g/m$^2$, and still even more preferably from 270 to 550 g/m$^2$, from the viewpoint of obtaining sufficient water-absorption ability even when a water-absorbent sheet composition of the present invention is used for an absorbent article. The water-absorbent resin is contained in an amount of preferably 100 g/m$^2$ or more, from the viewpoint of exhibiting sufficient water absorption ability as a water-absorbent sheet composition, thereby suppressing re-wetting, and the water-absorbent resin is contained in an amount of preferably 1000 g/m$^2$ or less, from the viewpoint of suppressing the generation of gel blocking phenomenon, exhibiting liquid diffusibility as a water-absorbent sheet composition, and further improving a liquid permeation rate.

The resin ratio (mass ratio) of the primary absorbent layer/secondary absorbent layer is preferably within the range of from primary absorbent layer/secondary absorbent layer=95/5 to 55/45, more preferably with the range of from primary absorbent layer/secondary absorbent layer=95/5 to 60/40, even more preferably within the range of from primary absorbent layer/secondary absorbent layer=95/5 to 70/30, and still even more preferably within the range of from primary absorbent layer/secondary absorbent layer=95/5 to 80/20. The primary absorbent layer/secondary absorbent layer is in a ratio of preferably 95/5 or less, from the viewpoint of sufficiently exhibiting water absorbency of a secondary absorbent layer, thereby preventing liquid leakage, and the primary absorbent layer/secondary absorbent layer is preferably in a ratio of 55/45 or more, from the viewpoint of increasing dry feel of the primary absorbent layer after liquid absorption.

The absorbency of the water-absorbent sheet composition of the present invention is influenced by the water absorbency of the water-absorbent resin used. Therefore, it is preferable that the water-absorbent resin to be used in the present invention is those selected with optimal ranges in water absorption properties such as water absorption capacity (water-retention capacity), and water absorption rate of the water-absorbent resin, by taking the constitution of each component of the water-absorbent sheet composition or the like into consideration. Therefore, in the water-absorbent resin used in the present invention, the kinds of the water-absorbent resin of the primary absorbent layer and the kinds of the water-absorbent resin of the secondary absorbent layer may be identical to or different from each other.

In the present specification, the water-retention capacity of the water-absorbent resin is evaluated as a water-retention capacity of saline solution. The water-absorbent resin has a water-retention capacity of saline solution of preferably 25 g/g or more, more preferably from 25 to 60 g/g, and even more preferably from 30 to 50 g/g, from the viewpoint of absorbing a liquid in a larger amount, and preventing the gel blocking phenomenon while keeping the gel strong during absorption. The water-retention capacity of saline solution of the water-absorbent resin is a value obtainable by a measurement method described in Examples set forth below.

In the present specification, the water absorption rate of the water-absorbent resin is evaluated as a water absorption rate of saline solution. The water-absorbent resin has a water-absorption rate of saline solution of preferably from 2 to 70 s, more preferably from 3 to 60 s, and even more preferably from 3 to 55 s, from the viewpoint of speeding up the permeation rate of the water-absorbent sheet composition of the present invention, thereby preventing a liquid leakage upon use in an absorbent article. The water-absorption rate of the water-absorbent resin as used herein is a value obtainable by a measurement method described in Examples set forth below.

In the composition of the present invention, it is preferable that there is a positive difference in values between the water absorption rate of saline solution of a water-absorbent resin in the primary absorbent layer and the rate of that of the secondary absorbent layer. The greater the difference therebetween, effects of avoiding the stagnation of a liquid in the primary absorbent layer, to thereby increase dry feel, and preventing a liquid leakage are even more strongly exhibited. Specifically, (the rate of resin in the primary absorbent layer)−(the rate of resin in the secondary absorbent layer) is preferably 10 seconds or more, more preferably 15 seconds or more, and even more preferably 20 seconds or more. In order to accomplish the situation as mentioned above, for example, the kind of a water-absorbent resin used in the primary absorbent layer and the kind of a water-absorbent layer may be arranged to be different kinds.

The water-absorbent resin has a median particle size of preferably from 100 to 600 μm, more preferably from 150 to 550 μm, and even more preferably from 200 to 500 μm, from the viewpoint of preventing the scattering of the water-absorbent resin in the water-absorbent sheet composition, the gel blocking phenomenon during water absorption, and at the same time reducing the rugged feel of the water-absorbent sheet composition, thereby improving texture.

The adhesive includes, for example, rubber adhesives such as natural rubbers, butyl rubbers, and polyisoprene; styrenic elastomer adhesives such as styrene-isoprene block copolymers (SIS), styrene-butadiene block copolymers (SBS), styrene-isobutylene block copolymers (SIBS), and styrene-ethylene-butylene-styrene block copolymers (SEBS); ethylene-vinyl acetate copolymer (EVA) adhesives; ethylene-acrylic acid derivative copolymer adhesives such as ethylene-ethyl acrylate copolymer (EEA), and ethylene-butyl acrylate copolymer (EBA); ethylene-acrylic acid copolymer (EAA) adhesives; polyamide adhesives such as copolymer nylons and dimer acids-based polyamides; polyolefin adhesives such as polyethylenes, polypropylenes, atactic polypropylenes, and copolymeric polyolefins; polyester adhesives such as polyethylene terephthalate (PET), polybutylene terephthalate (PBT), and copolymeric polyesters; and acrylic adhesives, and these adhesives may be used together in two or more kinds. In the present invention, the ethylene-vinyl acetate copolymer adhesives, the styrenic elastomer adhesives, the polyolefinic adhesives, and the polyester adhesives are preferred, from the viewpoint of high adhesive strength, thereby making it possible to prevent exfoliation of a hydrophilic nonwoven fabric and scattering of the water-absorbent resin in the water-absorbent sheet composition. Further, the ethylene-vinyl acetate copolymer adhesives, the polyester adhesives, and the polyolefinic adhesives are more preferred, from the viewpoint of being convenient in handling and excellent in workability.

The adhesive has a melting temperature or a softening point of preferably from 60° to 180° C., and more preferably from 70° to 150° C., from the viewpoint of sufficiently fixing a water-absorbent resin to a nonwoven fabric, and at the same time preventing thermal deterioration or deformation of the nonwoven fabric. Here, in the water-absorbent sheet composition of the present invention, in the process of producing a water-absorbent sheet composition, after melting, the adhesive is adhered to a nonwoven fabric or a water-absorbent resin in a solid state by cooling the molten adhesive.

The adhesive in the water-absorbent sheet composition is contained in an amount preferably in the range of from 0.05 to 2.0 times, more preferably in the range of from 0.08 to 1.5 times, and even more preferably in the range of from 0.1 to 1.0 time the amount of the water-absorbent resin contained (mass basis). It is preferable that the adhesive is contained in an amount of 0.05 times or more, from the viewpoint of having sufficient adhesion, thereby preventing exfoliation of the hydrophilic nonwoven fabrics themselves or scattering of the water-absorbent resin, and increasing strength of a water-absorbent sheet composition. It is preferable that the adhesive is contained in an amount of 2.0 times or less, from the viewpoint of avoiding the inhibition of the swelling of the water-absorbent resin due to too strong adhesion to each other, thereby improving a permeation rate or liquid leakage of a water-absorbent sheet composition.

The absorbent layer contains a water-absorbent resin and an adhesive, and the absorbent layer is formed by, for example, evenly dispersing a mixed powder of a water-absorbent resin and an adhesive on a hydrophilic nonwoven fabric, and further overlaying with a water-permeable substrate, and subjecting overlaid layers to heat-and-pressure fixing near a melting temperature of the adhesive.

The hydrophilic nonwoven fabric is not particularly limited, as long as the hydrophilic nonwoven fabric is a known nonwoven fabric in the field of art. The hydrophilic nonwoven fabric includes nonwoven fabrics made of polyolefin fibers such as polyethylene (PE) and polypropylene (PP); polyester fibers such as polyethylene terephthalate (PET), polytrimethylene terephthalate (PTT), and polyethylene naphthalate (PEN); polyamide fibers such as nylon; rayon fibers, and other synthetic fibers; nonwoven fabrics produced by mixing cotton, silk, hemp, pulp (cellulose) fibers, or the like, from the viewpoint of liquid permeability, flexibility and strength upon forming into a sheet composition, and the hydrophilic nonwoven fabric may be a mixture of two or more kinds of fibers. In addition, its surface may be subjected to a hydrophilic treatment according to a known method, as occasion demands. The nonwoven fabric made of synthetic fibers is preferably used, from the viewpoint of increasing the strength of the water-absorbent sheet composition, and especially at least one member selected from the group consisting of rayon fibers, polyolefin fibers, polyester fibers, and mixtures thereof is preferred. The hydrophilic nonwoven fabric made of synthetic fibers may contain pulp fibers in a small amount to an extent that the thickness of the water-absorbent sheet composition would not increase.

The hydrophilic nonwoven fabric is preferably a nonwoven fabric having an appropriate basis weight and an appropriate thickness, from the viewpoint of giving the water-absorbent sheet composition of the present invention excellent liquid permeability, flexibility, strength and cushioning property, and speeding up the permeation rate of the water-absorbent sheet composition. The hydrophilic nonwoven fabric has a basis weight of preferably 25 $g/m^2$ or more, more preferably in the range of from 35 to 250 $g/m^2$, and even more preferably in the range of from 45 to 150 $g/m^2$. The hydrophilic nonwoven fabric has a thickness of preferably in the range of from 200 to 1500 μm, more preferably in the range of from 250 to 1200 μm, and even more preferably in the range of from 300 to 1000 μm.

As the water-permeable substrate, those having a water permeability index as defined by the method described in the present specification of from 20 to 90 are used. It is necessary that the water-permeable substrate is a material which appropriately permeates a subject liquid and appropriately diffuses in the substrate. Moreover, as the function of a water-permeable substrate, if water permeability is weighed with importance, gel blocking occurs, and if diffusion is weighed with importance, liquid leakage occurs, so that it is necessary to find a material with a proper balance to be used as a water-absorbent sheet composition. However, numerous factors such as hydrophilic property, basis weight, and thickness of a substrate must be taken into account, thereby making it very difficult find such a material.

The present inventors have found that a water-permeable substrate having a specified water permeability index is excellent in such a balance, and the present invention is accomplished thereby. The water-permeable substrate has a water permeability index in the range of from 20 to 90, more preferably from 30 to 85, even more preferably from 35 to 80, and still even more preferably from 40 to 75. The water-permeable substrate has a water permeability index of preferably 20 or more, from the viewpoint of suppressing excessive diffusion of the absorbed liquid, and the water-permeable substrate has a water permeability index of preferably 90 or less, from the viewpoint of suppressing excessive water permeation of the absorbed liquid. When the liquid diffusion is in excess, a secondary absorbent layer cannot be effectively used, so that a liquid leakage is likely to occur. On the other hand, when water permeation of the liquid is in excess, a primary absorbent layer cannot be effectively used, so that liquid is rapidly distributed in the secondary absorbent layer, thereby making it likely to cause gel blocking. Specific examples of preferred materials include at least one member selected from the group consisting of sanitary papers, nonwoven fabrics made of cellulose-containing synthetic fibers, nonwoven fabrics made of rayon-containing synthetic fibers, and nonwoven fabrics made of hydrophilically treated synthetic fibers.

The sanitary papers include, for examples, tissue paper, toilet paper, paper towel, and the like. The nonwoven fabrics made of cellulose-containing synthetic fibers include, for example, airlaid nonwoven fabrics made of pulp/PET/polyethylene (PE), pulp/PET/polypropylene (PP), pulp/PE/PP. The nonwoven fabrics made of rayon-containing synthetic fibers include, for example, spunlaid nonwoven fabrics made of rayon/PET, rayon/PE, or rayon/PET/PE. The nonwoven fabrics made of hydrophilically treated synthetic fibers include, for example, a polyolefin air-through nonwoven fabric of a polyolefin comprising PE, PP, or PE/PP coated with a hydrophilic surfactant such as a fatty acid ester-type nonionic surfactant or a polyglycerol fatty acid ester. Among them, the nonwoven fabrics made of rayon-containing synthetic fibers are more preferably used, from the viewpoint of the properties of the resulting water-absorbent sheet composition.

The thickness and the basis weight of the water-permeable substrate are not particularly limited. Exemplifying more preferred forms, the water-permeable substrate has a thickness of preferably from 150 to 1500 µm, more preferably from 200 to 1000 µm, and even more preferably from 250 to 800 µm. The water-permeable substrate has a basis weight of preferably 10 g/m² or more, more preferably 15 g/m² or more, even more preferably in the range of from 25 to 250 g/m², and still even more preferably in the range of from 40 to 150 g/m². The water-permeable substrate preferably has a thickness of 1500 µm or less and a basis weight of 250 g/m² or less, from the viewpoint of thinning a water-absorbent sheet composition, and on the other hand, and the water-permeable substrate preferably has a thickness of 150 µm or more and a basis weight of 10 g/m² or more, from the viewpoint of obtaining sufficient strength against stretching and twisting during the production and upon use of a water-absorbent sheet composition.

The water-absorbent sheet composition of the present invention can be produced by a method, for example, as described in a method as described hereinbelow, utilizing a conventional method.

(a) A mixed powder of a water-absorbent resin and an adhesive is evenly dispersed over a hydrophilic nonwoven fabric, a water-permeable substrate is further overlaid thereto, and the overlaid layers are subjected to heat-and-pressure fusing near a melting temperature of an adhesive to give an intermediate product. The mixed powder is dispersed to this intermediate product in the same manner as the above, and the hydrophilic nonwoven fabric is again subjected to heat-and-pressure fusing.

(b) A mixed powder of a water-absorbent resin and an adhesive is evenly dispersed over a hydrophilic nonwoven fabric, a water-permeable substrate is further overlaid thereto, the mixed powder is then dispersed again thereto, a hydrophilic nonwoven fabric is overlaid thereon, and the overlaid layers are entirely subjected to heat-and-pressure fusing.

(c) A mixed powder of a water-absorbent resin and an adhesive is evenly dispersed over a hydrophilic nonwoven fabric, the layers are passed through a heated furnace to fix to an extent that the powder is not scattered, a water-permeable substrate is overlaid thereon, a mixed powder is then dispersed thereto again, a hydrophilic nonwoven fabric is overlaid thereon, and the overlaid layers are entirely subjected to heat-and-pressure fusing.

(d) An adhesive is melt-coated on a hydrophilic nonwoven fabric, immediately thereafter a water-absorbent resin is evenly dispersed to form a layer, and an adhesive is further melt-coated from an upper part and overlaid with a water-permeable substrate to give an intermediate product. This intermediate product is again subjected to the same procedures as mentioned above.

Here, among the methods exemplified in (a) to (d), the compositions can be produced by selecting methods of adhering a primary absorbent layer and a secondary absorbent layer, to be used in combination. The water-absorbent sheet composition may be subjected to emboss treatment during heat-and-pressure fusing in the production of a sheet or after the production of the sheet, for the purposes of improving the feel and improving strength of the water-absorbent sheet composition.

In addition, the water-absorbent sheet composition of the present invention may properly be formulated with an additive such as a deodorant, an anti-bacterial agent, or a gel stabilizer.

The water-absorbent sheet composition of the present invention has one feature in the aspect of enabling thinning of the composition. When the use in absorbent articles is taken into consideration, the water-absorbent sheet has a thickness, on a dry basis, of preferably 5 mm or less, more preferably 4 mm or less, even more preferably 3 mm or less, and still even more preferably from 1.0 to 2.5 mm.

Further, the water-absorbent sheet composition of the present invention has one feature in that a liquid has a fast permeation rate, and the water-absorbent sheet composition has a total permeation rate of preferably 100 seconds or less, more preferably 90 seconds or less, and even more preferably 80 seconds or less, when taking the use as an absorbent article into consideration.

Further, the water-absorbent sheet composition of the present invention has one feature in that a liquid has smaller liquid leakage, and the water-absorbent sheet composition has a leakage index of preferably 200 or less, more preferably 100 or less, and even more preferably 50 or less, when taking the use as an absorbent article into consideration.

Further, since the water-absorbent sheet composition of the present invention has a very small amount of a material derived from nature, consideration has been made to the environment while having high performance in thickness, permeation rate, and a leakage index as mentioned above. The proportion of the natural material is preferably 30% or less, more preferably 20% or less, and even more preferably 15% or less. The proportion of the natural material is calculated by dividing a total content of pulp, cotton and the like contained in very small amounts as the constituents of the water-absorbent sheet composition by mass of the water-absorbent sheet composition.

A water-absorbent sheet composition satisfying all the properties as mentioned above is very highly preferable in consideration of its use as an absorbent article.

Next, the structure of the water-absorbent sheet composition of the present invention will be explained by referring to FIG. 1. Here, FIG. 1 is an enlarged cross-sectional view schematically showing one example of the structure of a water-absorbent sheet composition of the present invention.

A water-absorbent sheet composition 51 shown in FIG. 1 comprises a primary absorbent layer 53 containing a water-absorbent resin 52 and an adhesive, and a secondary absorbent layer 55 containing a water-absorbent resin 54 and an adhesive. Here, the primary absorbent layer refers to a side to which a liquid to be absorbed is fed upon the preparation of an absorbent article using the water-absorbent sheet composition, and the secondary absorbent layer refers to a side opposite to the primary absorbent layer interposed with a water-permeable substrate 56.

Moreover, a primary absorbent layer 53 and a secondary absorbent layer 55 are divided by a water-permeable substrate 56, and a water-absorbent sheet composition 51 comprises a primary absorbent layer 53, a secondary absorbent layer 55, a water-permeable substrate 56, and front and back two layers made of a hydrophilic nonwoven fabric 57 positioned at each of the outer surface of the primary absorbent layer 53 and the secondary absorbent layer 55, which is a structure in which the absorbent layers are sandwiched by two or more sheets of hydrophilic nonwoven fabrics 57.

The absorbent article of the present invention has a structure in which a water-absorbent sheet composition of the present invention is sandwiched between a liquid-permeable sheet and a liquid-impermeable sheet. The absorbent article includes, for example, disposable diapers, incontinence pads, sanitary napkins, pet sheets, drip sheets for foods, water blocking materials for electric power cables, and the like. Further, as the liquid-permeable sheet and the liquid-impermeable sheet, known ones in the technical field of the absorbent articles can be used without particular limitations. The absorbent article can be produced by a known method.

EXAMPLES

The present invention will be specifically described hereinbelow by the Examples, without intending to limit the scope of the present invention thereto.

The properties of the water-absorbent resin and the water-absorbent sheet composition were measured in accordance with the following methods.

<Water-Retention Capacity of Saline Solution of Water-Absorbent Resin>

The amount 2.0 g of water-absorbent resin was weighed in a cotton bag (Cottonbroad No. 60, width 100 mm×length 200 mm), and placed in a 500 mL-beaker. Physiological saline (0.9% by mass aqueous solution of sodium chloride, hereinafter referred to the same) was poured into the cotton bag in an amount of 500 g at one time, and the physiological saline was dispersed so as not to cause an unswollen lump of the water-absorbent resin. The upper part of the cotton bag was tied up with a rubber band, and the cotton bag was allowed to stand for 1 hour, to sufficiently make the water-absorbent resin swell. The cotton bag was dehydrated for 1 minute with a dehydrator (manufactured by Kokusan Enshinki Co., Ltd., product number: H-122) set to have a centrifugal force of 167 G. The mass Wa (g) of the cotton bag containing swollen gels after the dehydration was measured. The same procedures were carried out without adding water-absorbent resin, and the empty mass Wb (g) of the cotton bag upon wetting was measured. The water-retention capacity of saline solution of the water-absorbent resin was calculated from the following formula.

Water-Retention Capacity of Saline Solution(g/g) of Water-Absorbent Resin=$[Wa-Wb]$(g)/Mass(g) of Water-Absorbent Resin <Water Absorption Rate of Saline Solution of Water-Absorbent Resin>

This test was conducted in a room temperature-controlled to 25°±1° C. The amount 50±0.1 g of physiological saline was weighed out in a 100 mL beaker, and a magnetic stirrer bar (8 mmϕ×30 mm, without a ring) was placed therein. The beaker was immersed in a thermostat, of which liquid temperature was controlled to 25°±0.2° C. Next, the beaker was placed over the magnetic stirrer so that a vortex was generated in physiological saline at a rotational speed of 600 r/min, the water-absorbent resin was then quickly added in an amount of 2.0±0.002 g to the above beaker, and the time period (seconds) from a point of addition of the water-absorbent resin to a point of convergence of the vortex of the liquid surface was measured with a stopwatch, which was defined as a water absorption rate of the water-absorbent resin.

<Median Particle Size of Water-Absorbent Resin>

Unless specified otherwise, the particle size of the water-absorbent resin is defined as a median particle size, and measured as follows. An amorphous silica (Sipernat 200, Degussa Japan) was mixed in an amount of 0.5 g as a lubricant with 100 g of a water-absorbent resin.

The above-mentioned water-absorbent resin particles were allowed to pass though a JIS standard sieve having a sieve opening of 250 μm, and a median particle size was measured using a combination of sieves of (A) in a case where the particles are allowed to pass in an amount of 50% by mass or more, or a combination of sieves of (B) in a case where 50% by mass or more of the particles remain on the sieve.

(A) JIS standard sieves, a sieve having an opening of 425 μm, a sieve having an opening of 250 μm, a sieve having an opening of 180 μm, a sieve having an opening of 150 μm, a sieve having an opening of 106 μm, a sieve having an opening of 75 μm, a sieve having an opening of 45 μm, and a receiving tray were combined in order from the top.

(B) JIS standard sieves, a sieve having an opening of 850 μm, a sieve having an opening of 600 μm, a sieve having an opening of 500 μm, a sieve having an opening of 425 μm, a sieve having an opening of 300 μm, a sieve having an opening of 250 μm, a sieve having an opening of 150 μm, and a receiving tray were combined in order from the top.

The above-mentioned water-absorbent resin particles were placed on an uppermost sieve of the combined sieves, and shaken for 20 minutes with a rotating and tapping shaker machine to classify the particles.

After classification, the relationships between the opening of the sieve and an integral of a mass percentage of the water-absorbent resin remaining on the sieve were plotted on a logarithmic probability paper by calculating the mass of the water-absorbent resin remaining on each sieve as a mass percentage to an entire amount, and accumulating the mass percentages in order, starting from those having larger particle diameters. A particle diameter corresponding to a 50% by mass cumulative mass percentage is defined as a median particle size by joining the plots on the probability paper in a straight line.

<Measurement of Thickness of Water-Absorbent Sheet Composition>

The thickness of the resulting water-absorbent sheet composition was measured using a thickness measurement instrument (manufactured by Kabushiki Kaisha Ozaki Seisakusho, model number: J-B). As the measurement sites, three sites were arbitrarily determined in a lengthwise direction, on the left end, the center, and the right end; for example, in a water-absorbent sheet composition of 10 cm×30 cm, the left end was set at a site 3 cm away from the left side, the center was set at a site 15 cm away therefrom, and the right end was set at a site 27 cm away therefrom. As the width direction, a uniform central part was measured.

The measurement value for thickness was obtained by measuring three times at each site and averaging the values for each site. Further, the values at the left end, the center, and the right end were averaged, to give a thickness of an overall water-absorbent sheet composition.

<Water Permeability Index of Water-Permeable Substrate>

Figure 2:
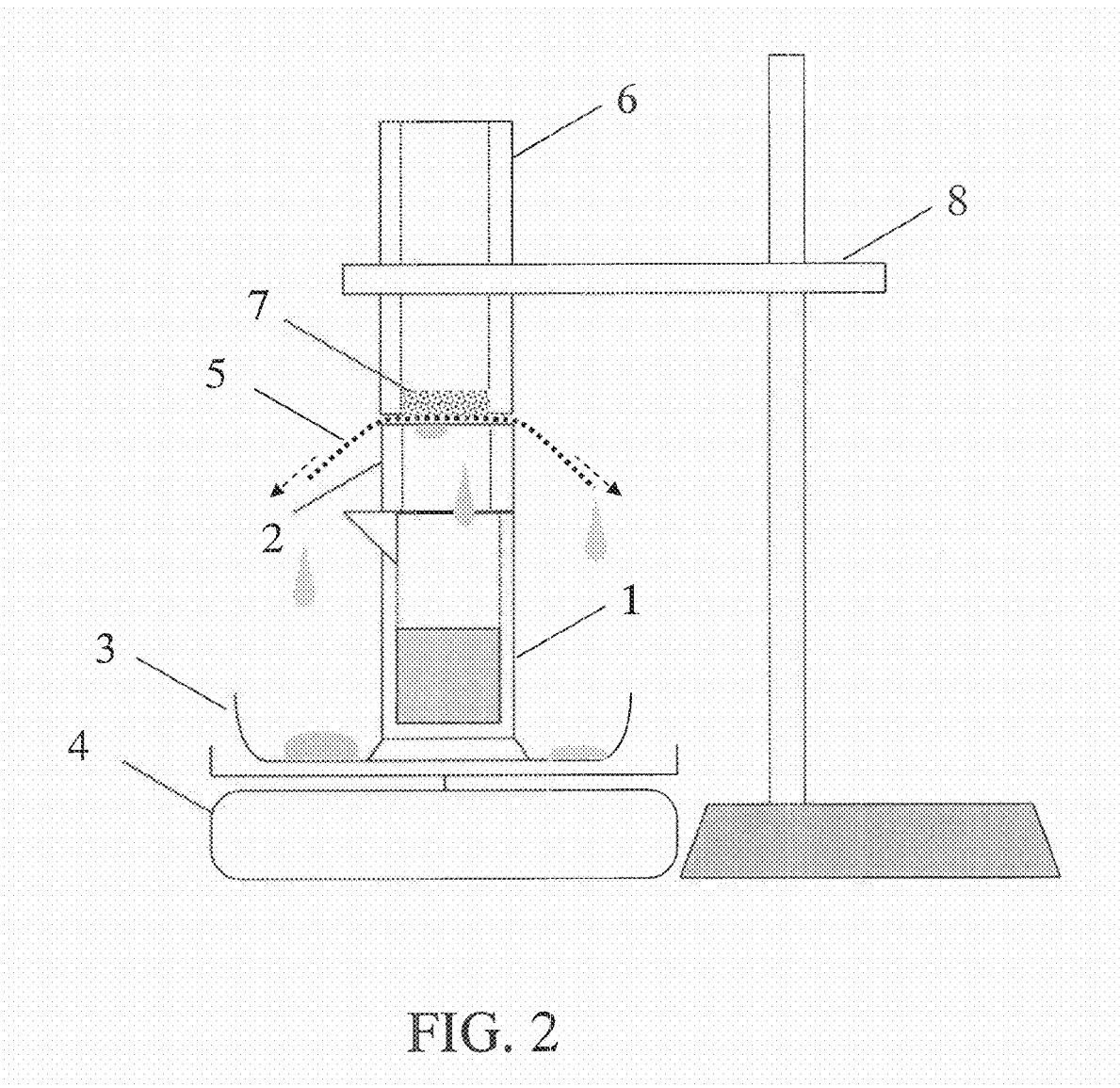
FIG. 2 is a schematic view of an apparatus used for obtaining a water permeability index of a water-permeable substrate.

The water permeability index of a water-permeable substrate was obtained using an apparatus shown in FIG. 2.

An acrylic cylinder (inner diameter: 25 mmϕ, thickness: 5 mm, height: about 30 mm) was fixed as a spacer 2 in an upper part of a 100 mL graduated cylinder 1 (inner diameter: 27 mmϕ), and the cylinder was placed on a balance 4 together with a metallic tray 3. A water-permeable substrate 5 to be measured, carefully cut into a size of 10 cm×10 cm so that fibers would not be spread among each other was placed at the central part of the pore of the spacer 2, and the indication of the balance 4 was compensated to zero. A acrylic cylinder 6 (inner diameter: 25 mmϕ), height: about 15 cm, roughness of glass filter: G1) equipped with a glass filter 7 as a supplying inlet from the upper part of the spacer 2 was placed, and held with a clamp 8 while keeping the leveling of the supplying inlet, and the height was subjected to minor adjustment so that a load of the mass applied to the supplying inlet of the acrylic cylinder 6 would be 15 g±2 g. The water-permeable substrate 5 was in a state gently pressed over an entire side of a circular side of the supplying inlet of the acrylic cylinder 6.

The water permeability index using such an apparatus was measured by the following procedures. One-hundred milliliters of a test solution having the same composition as that used in the <Evaluations of Total Permeation Rate and Amount of Re-Wet of Water-Absorbent Sheet Composition> described later was measured, and placed in the supplying inlet while keeping the liquid height to 4 to 6 cm in the acrylic cylinder.

After the entire amount was allowed to permeate water, and a liquid volume (X mL) stored in the internal of the graduated cylinder 1 was measured. A test solution diffused to the external part via a water-permeable substrate 5 was collected in a metallic tray 3 (for those that did not terminate water permeation within 10 minutes from the beginning of supplying, a liquid volume (X mL) at a point of 10 minutes passed being measured). The numerical value X of the liquid volume (X mL) was defined as a water permeability index of the water-permeable substrate. Here, Table 1 lists a water permeability index of a water-permeable substrate used in Examples and the like.

<Strength of Water-Absorbent Sheet Composition>

The strength of the water-absorbent sheet composition was evaluated in accordance with the following method.

Figure 3:
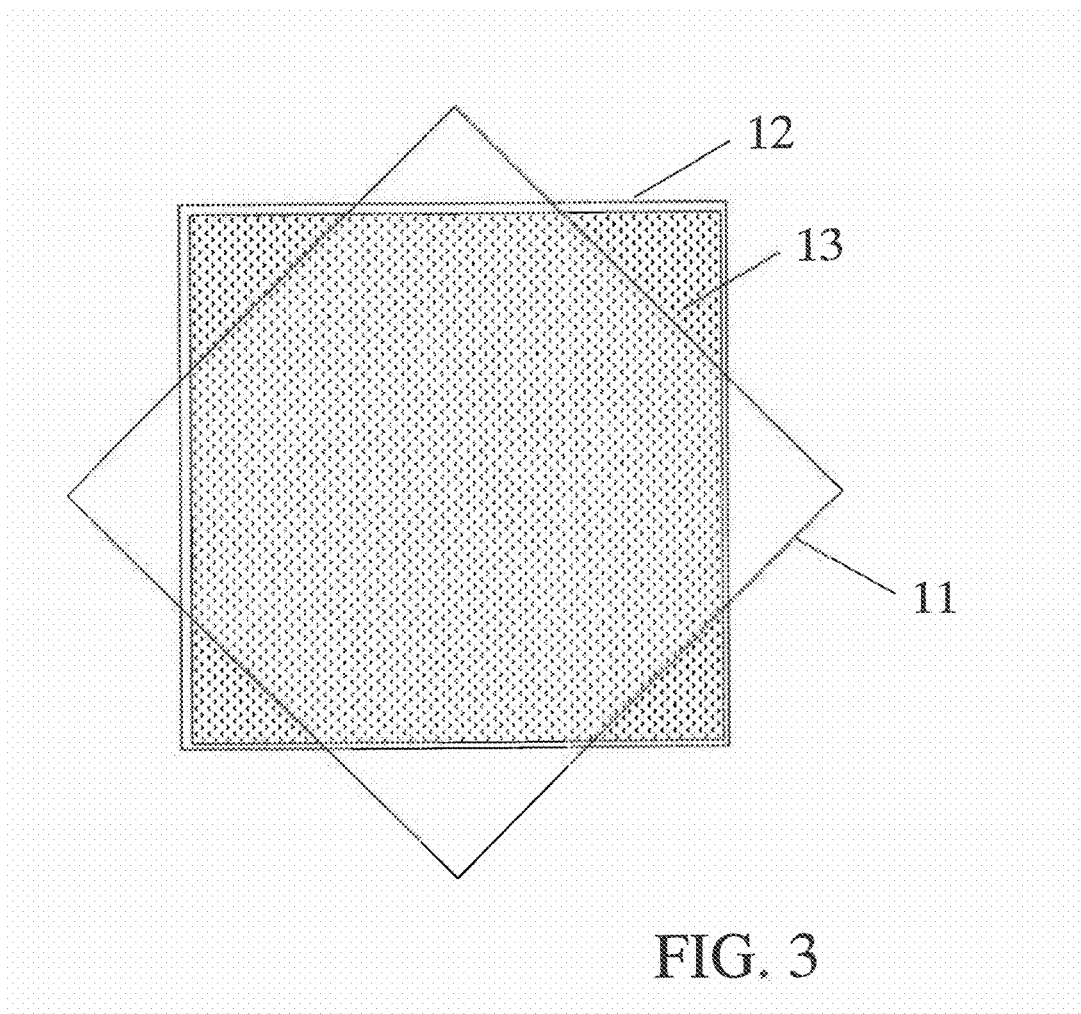
FIG. 3 is a schematic view showing arrangements of a water-absorbent sheet composition and an acrylic plate, for evaluating strength of the water-absorbent sheet composition.

The resulting water-absorbent sheet composition was cut into a size of 10 cm×10 cm. Next, the entire side of each of one side of two pieces of acrylic plates of 10 cm×10 cm (mass about 60 g) was adhered with a double-sided adhesive tape. As shown in FIG. 3, the acrylic plates were pressed in a manner that the diagonal lines of acrylic plates 11, 12 form 45 degrees in angle, sandwiching from top and bottom to fix so that the double-sided adhesive tape faces the side of the water-absorbent sheet composition.

The strength-test pieces of the water-absorbent sheet composition prepared in the manner as described above were placed on a metallic tray of sieves, used in the section of the above-mentioned <Median Particle Size of Water-Absorbent Resin>, and a lid was put thereon. Thereafter, the lidded vessel was tapped with rotations with a rotating and tapping shaker machine for 3 minutes (at this time, a few layers of mesh sieves may be provided as a spacer between the tray and the tapping machine). The strength of the water-absorbent sheet composition was evaluated based on the external appearance after tapping in accordance with the following criteria.

○: The water-absorbent sheet composition showed no changes in external appearance, and did not easily move even when the acrylic plates were tried to be displaced.

Δ: The water-absorbent sheet composition showed no changes in external appearance, but the water-absorbent sheet composition was removed from the center when the acrylic plates were displaced.

x: The water-absorbent sheet composition was split in two from the center, and the contents were scattered.

A simple water-absorbent article was prepared using the resulting water-absorbent sheet composition, and its physical properties were measured.

The preparation conditions at this time were set to have the same conditions for all the water-absorbent sheet compositions in Examples and Comparative Examples.

<Evaluations of Total Permeation Rate and Amount of Re-wet of Water-Absorbent Sheet Composition>

A rectangular strip of a water-absorbent sheet composition of 10×30 cm, cut in a manner that a longitudinal direction thereof is to be in a length direction (machine feeding direction) of the hydrophilic nonwoven fabric, was used as a sample.

In a 10 L vessel were placed 60 g of sodium chloride, 1.8 g of calcium chloride dihydrate, 3.6 g of magnesium chloride hexahydrate, and a proper amount of distilled water to completely dissolve. Next, 15 g of an aqueous 1% by mass poly(oxyethylene)isooctylphenyl ether solution was added thereto, and distilled water was further added to adjust the weight of the overall aqueous solution to 6000 g. Thereafter, the mixed solution was colored with a small amount of Blue No. 1 to prepare a test solution.

On an upper part of a sample (water-absorbent sheet composition) was placed a polyethylene air-through style porous liquid-permeable sheet having the same size as the sample (10×30 cm) and a basis weight of 22 g/m². In addition, underneath the sample was placed a polyethylene liquid-impermeable sheet having the same size and basis weight as the sheet, to prepare a simple body liquid-absorbent article. A cylindrical cylinder having an inner diameter of 3 cm was placed near the central section of this body liquid-absorbent article, and a 50 mL test solution was supplied thereto at one time. At the same time, a time period until the test solution was completely permeated into the body liquid-absorbent article was measured with a stopwatch, which is referred to as a first permeation rate (sec). Next, the same procedures were carried out 30 minutes thereafter and 60 minutes thereafter, to measure second and third permeation rates (sec). A total of the number of seconds for the first to third permeation rates is referred to as a total permeation rate.

After 120 minutes from the start of the feeding of the first test liquid, the cylinder was removed, filter papers of 10 cm each side, of which mass was previously measured (Wg (g), about 70 g), were stacked near the liquid feeding position of the body liquid-absorbent article, and a 5 kg weight having a size of 10 cm×10 cm was placed thereon. After 5 minutes of applying a load, the mass (Wh (g)) of the filter papers was measured, and an increased mass was defined as the amount of re-wet (g) as follows.

$$\text{Amount of Re-wet(g)} = Wh - Wg$$

<Slope Leakage Test>

Figure 4:
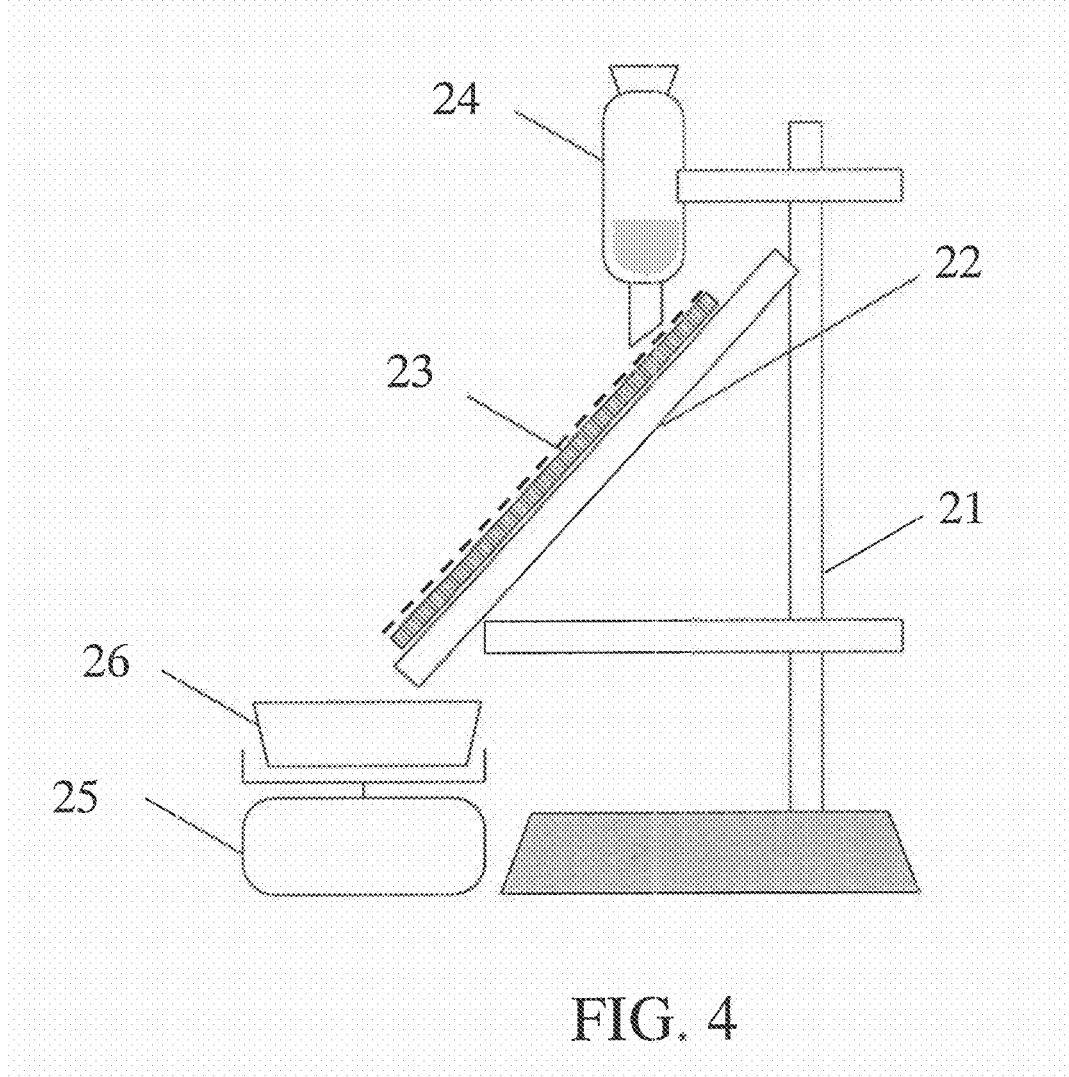
FIG. 4 is a schematic view of an apparatus used for carrying out a slope leakage test.

A slope leakage test was conducted using an apparatus shown in FIG. 4.

Schematically, a mechanism is as follows. A commercially available stand 21 for experimental facilities was used to slope an acrylic plate 22 and fixed, the above-mentioned test solution was then supplied to a water-absorbent sheet composition 23 placed on the acrylic plate from a dropping funnel 24 positioned vertically above the sheet composition, and a leakage amount was measured with a balance 25. The detailed specifications are given hereinbelow.

An acrylic plate 22 has a length in the direction of the slope plane of 45 cm, and fixed so that an angle formed with a stand 21 against the horizontal is 45°±2°. The acrylic plate 22 had a width of about 100 cm and a thickness of about 1 cm, and plural water-absorbent sheet compositions 23 could be concurrently measured. The acrylic plate 22 had a smooth surface, so that a liquid was not detained or absorbed to the plate.

A dropping funnel 24 was fixed at a position vertically above the sloped acrylic plate 22 using a stand 21. The dropping funnel 24 had a volume of 100 mL, and an inner diameter of a tip end portion of about 4 mmφ, and an aperture of the cock was adjusted so that a liquid was supplied at a rate of 8 mL/seconds.

A balance 25 on which a metallic tray 26 was placed was set at a lower part of the acrylic plate 22, and all the test solutions flowing down the acrylic plate was received as leakage, and its mass was recorded to the accuracy of 0.1 g.

A slope leakage test using an apparatus as described above was carried out in accordance with the following procedures. The mass of a water-absorbent sheet composition 23 cut into a size of a length of 30 cm and a width of 10 cm was measured, and an air through-style polyethylene liquid permeable nonwoven fabric (basis weight: 22 g/m$^2$) of the same size was attached from an upper part thereof, and further a polyethylene liquid impermeable nonwoven fabric having the same basis weight of the same size was attached from a lower part thereof to prepare a simple absorbent article. The simple absorbent article was adhered on the acrylic plate 22 (in order not to stop leakage intentionally, the bottom end of the water-absorbent sheet composition 23 was not adhered to the acrylic plate 22).

Marking was put on the water-absorbent sheet composition 23 at a position 2 cm away in a downward direction from a top end thereof, and a supplying inlet for the dropping funnel 24 was fixed so that the inlet was positioned at a distance 8 mm±2 mm vertically above the marking.

A balance 25 was turned on, and tared so that the indication was zero, and thereafter 80 mL of the above-mentioned test solution was supplied at one time to the dropping funnel 24. An amount of liquid poured into a metallic tray 26 after the test solution was allowed to flow over a sloped acrylic plate 22 without being absorbed into a water-absorbent sheet composition 23 was measured, and this amount of liquid is referred to a first leakage amount (mL). The numerical value for this first leakage amount (mL) is denoted as LW1.

Second and third test solutions were supplied in 10-minute intervals from the beginning of the first supply, and second and third leakage amounts (mL) were measured, and the numerical values therefor are respectively denoted as LW2 and LW3.

Next, a leakage index was calculated in accordance with the following equation. The more the index approaches to zero, the smaller the leakage amount at a slope of a water-absorbent sheet composition, especially an initial leakage amount, whereby it is judged to be an excellent water-absorbent sheet composition.

Leakage Index: $L = LW1 \times 10 + LW2 \times 5 + LW3$

EXAMPLE 1

A roller spreader (manufactured by HASHIMA CO., LTD., SINTERACE M/C) was charged at its supplying inlet with a mixture prepared by homogeneously mixing 55 parts by mass of an ethylene-vinyl acetate copolymer (melting temperature: 95° C.) as an adhesive and 270 parts by mass of a sodium polyacrylate crosslinked product (manufactured by Sumitomo Seika Co., Ltd., AQUAKEEP SA55SX-II, median particle size: 360 µm; water-absorption rate of saline solution: 42 seconds, water retention capacity of saline solution: 35 g/g) as a water-absorbent resin. On the other hand, a hydrophilic nonwoven fabric made of rayon having a width of 30 cm (basis weight: 45 g/m$^2$, rayon content: 100%) was spread over a conveyor at the bottom part of the spreader. Next, the spreading roller and the bottom part conveyor were operated, thereby allowing the above-mentioned mixture to evenly overlay over the above-mentioned nonwoven fabric at a basis weight of 325 g/m$^2$.

The overlaid product obtained was pressed from a top part with a water-permeable substrate tissue paper (basis weight: 17 g/m$^2$), and heat-fused with a thermal laminating machine (manufactured by HASHIMA CO., LTD., straight linear fusing press HP-600LF) set at 130° C. to integrate, to give an intermediate product of a water-absorbent sheet composition. This intermediate product was placed again on the conveyor of a roller spreader, and the spreading roller and the bottom part conveyor were operated, thereby allowing the above-mentioned mixture to evenly overlay over the above-mentioned nonwoven fabric at a basis weight of 78 g/m$^2$.

The overlaid product obtained was pressed from a top part with the above-mentioned hydrophilic nonwoven fabric, and heat-fused with a thermal laminating machine (manufactured by HASHIMA CO., LTD., straight linear fusing press HP-600LF) set at 130° C. to integrate, to give a water-absorbent sheet composition. The cross section of the structure of the resulting water-absorbent sheet composition, as schematically shown, had a structure as shown in FIG. 1.

The water-absorbent sheet composition was cut into a given size to measure the properties of the water-absorbent sheet composition. The results are shown in Table 2.

EXAMPLES 2 TO 6

A water-absorbent sheet composition was obtained in the same manner as in Example 1, except that materials listed in Table 1 were used in place of rayon as a hydrophilic nonwoven fabric, tissue paper as a water-permeable substrate, and an ethylene-vinyl acetate copolymer as an adhesive, in Example 1. Incidentally, in Examples 3 and 6, only the water-absorbent resin used in the secondary absorbent layer was changed to a sodium polyacrylate crosslinked product (manufactured by Sumitomo Seika Co., Ltd., AQUAKEEP 10SH-PB, median particle size: 320 µm, water absorption rate of saline solution: 3 seconds, water-retention capacity of saline solution: 42 g/g), without changing the water-absorbent resin used in the primary absorbent layer. In addition, in Examples 5 and 6, the amount of the water-absorbent resin and the amount of the adhesive were changed as listed in Table 1. The details of other materials are given hereinbelow.

Rayon-PET: basis weight: 50 g/m$^2$, rayon content: 70%
Hydrophilically Treated PE-PP: basis weight: 35 g/m$^2$, subjected to hydrophilic treatment with a surfactant on the side of a primary absorbent layer
Cellulose-containing PET/PE: basis weight: 45 g/m$^2$, cellulose content: 50%
Polyester adhesive: copolymer polyester, melting temperature: 80° C. (heating temperature of thermal fusion: 100° C.)
Polyethylene adhesive: low-density polyethylene, melting temperature: 107° C. (heating temperature of thermal fusion: 140° C.)

The water-absorbent sheet composition obtained was cut into a given size to measure the properties of the water-absorbent sheet composition. The results are shown in Table 2.

COMPARATIVE EXAMPLE 1

A roller spreader (manufactured by HASHIMA CO., LTD., SINTERACE M/C) was charged at its supplying inlet with a mixture prepared by homogeneously mixing 55 parts by mass of an ethylene-vinyl acetate copolymer (melting temperature: 95° C.) as an adhesive and 330 parts by mass of a sodium polyacrylate crosslinked product (manufactured by Sumitomo Seika Co., Ltd., AQUAKEEP SA55SX-II, median particle size: 360 μm; water-absorption rate of saline solution: 42 seconds, water retention capacity of saline solution: 35 g/g) as a water-absorbent resin. On the other hand, a hydrophilic nonwoven fabric made of rayon having a width of 30 cm (basis weight: 45 g/m², rayon content: 100%) was spread over a conveyor at the bottom part of the spreader. Next, the spreading roller and the bottom part conveyor were operated, thereby allowing the above-mentioned mixture to evenly overlay over the above-mentioned nonwoven fabric at a basis weight of 385 g/m².

The overlaid product obtained was pressed from a top part with the above-mentioned hydrophilic nonwoven fabric, and heat-fused with a thermal laminating machine (manufactured by HASHIMA CO., LTD., straight linear fusing press HP-600LF) set at 130° C. to integrate, to give a water-absorbent sheet composition.

The water-absorbent sheet composition was cut into a given size to measure the properties of the water-absorbent sheet composition. The results are shown in Table 2.

COMPARATIVE EXAMPLES 2 AND 3

A water-absorbent sheet composition was obtained in the same manner as in Example 1, except that materials listed in Table 1 were used in place of rayon as a hydrophilic nonwoven fabric, tissue paper as a water-permeable substrate, and an ethylene-vinyl acetate copolymer as an adhesive, in Example 1. Incidentally, in Comparative Example 3, only the water-absorbent resin used in the secondary absorbent layer was changed to a sodium polyacrylate crosslinked product (manufactured by Sumitomo Seika Co., Ltd., AQUAKEEP 10SH-PB, median particle size: 320 μm, water absorption rate of saline solution: 3 seconds, water-retention capacity of saline solution: 42 g/g).

COMPARATIVE EXAMPLE 4

A water-absorbent sheet composition was obtained in the same manner as in Example 1, except that rayon-PET was used in place of rayon as a hydrophilic nonwoven fabric, that rayon was used in place of tissue paper as a water-permeable substrate, and that an ethylene-vinyl acetate copolymer was not used at all as an adhesive for the roller spreader. Here, the basis weight of the component fed from the spreader (only a water-absorbent resin) was 270 g/m² for the first run, and 65 g/m² for the second run. The water-absorbent sheet composition was cut into a given size to measure the properties of the water-absorbent sheet composition. The results are shown in Table 2.

COMPARATIVE EXAMPLE 5

A water-absorbent sheet composition was obtained in the same manner as in Comparative Example 4, except that the basis weight of rayon as a water-permeable substrate was 20 g/m², and that the basis weight of the component fed from the spreader (only a water-absorbent resin) was 20 g/m² for the first run, and 50 g/m² for the second run, in Comparative Example 4. The water-absorbent sheet composition was cut into a given size to measure the properties of the water-absorbent sheet composition. The results are shown in Table 2.

TABLE 1

| | Hydrophilic Nonwoven Fabric | | Water-Permeable Substrate | | | Water-Absorbent Resin (g/m²) | |
|---|---|---|---|---|---|---|---|
| | Top | Bottom | Kind | g/m² | Index | Primary | Secondary |
| Example 1 | Rayon | Rayon | Tissue Paper | 17 | 40 | 270 | 65 |
| Example 2 | Rayon-PET | Rayon-PET | Rayon-PET | 50 | 60 | 270 | 65 |
| Example 3 | Rayon-PET | Rayon-PET | Rayon-PET | 45 | 75 | 270 | 65 |
| Example 4 | Rayon | Rayon | Hydrophilically Treated PE-PP | 35 | 65 | 270 | 65 |
| Example 5 | Rayon-PET | Rayon-PET | Cellulose-Containing PET/PE | 45 | 50 | 350 | 150 |
| Example 6 | Rayon-PET | Rayon-PET | Rayon-PET | 50 | 60 | 160 | 40 |
| Comparative Example 1 | Rayon | Rayon | — | — | — | 330 | — |
| Comparative Example 2 | Rayon-PET | Rayon-PET | PE-PP | 14 | 96 | 270 | 65 |
| Comparative Example 3 | Rayon-PET | Rayon-PET | PP | 40 | 12 | 270 | 65 |
| Comparative Example 4 | Rayon-PET | Rayon-PET | Rayon | 45 | 75 | 270 | 65 |
| Comparative Example 5 | Rayon-PET | Rayon-PET | Rayon | 20 | 95 | 20 | 50 |

| | Water-Absorbent Resin (g/m²) | Adhesive (g/m²) | | | |
|---|---|---|---|---|---|
| | Ratio* | Kind | Primary | Secondary | Content** |
| Example 1 | 81/19 | Ethylene-Vinyl Acetate | 55 | 13 | 0.20 |
| Example 2 | 81/19 | Polyester | 55 | 13 | 0.20 |
| Example 3 | 81/19 | Polyester | 55 | 13 | 0.20 |
| Example 4 | 81/19 | Ethylene-Vinyl Acetate | 55 | 13 | 0.20 |
| Example 5 | 73/27 | Polyethylene | 60 | 25 | 0.17 |
| Example 6 | 80/20 | Polyester | 15 | 5 | 0.10 |

TABLE 1-continued

| | | | | | |
|---|---|---|---|---|---|
| Comparative Example 1 | — | Ethylene-Vinyl Acetate | 55 | — | 0.17 |
| Comparative Example 2 | 81/19 | Polyester | 55 | 13 | 0.20 |
| Comparative Example 3 | 81/19 | Polyester | 55 | 13 | 0.20 |
| Comparative Example 4 | 81/19 | — | — | — | — |
| Comparative Example 5 | 29/71 | — | — | — | — |

*Ratio of primary absorbent layer to secondary absorbent layer, i.e. primary/secondary, of water-absorbent resin (mass ratio)
**Content of adhesive (content based on water-absorbent resin (mass basis))

TABLE 2

| | Thickness (mm) | Permeation Rate (sec) | | | | Amount of Rewet (g) | Slope Leakage Test | | | Index | Strength of Water-Absorbent Sheet |
|---|---|---|---|---|---|---|---|---|---|---|---|
| | | 1 | 2 | 3 | Total | | 1 | 2 | 3 | | |
| Example 1 | 1.6 | 30 | 21 | 24 | 75 | 2.6 | 3 | 0 | 0 | 30 | ○ |
| Example 2 | 1.4 | 32 | 22 | 23 | 77 | 1.4 | 2 | 0 | 0 | 20 | ○ |
| Example 3 | 1.4 | 26 | 18 | 23 | 67 | 2.3 | 0 | 0 | 0 | 0 | ○ |
| Example 4 | 1.5 | 36 | 21 | 15 | 72 | 2.8 | 4 | 0 | 0 | 40 | ○ |
| Example 5 | 1.9 | 38 | 26 | 25 | 89 | 0.7 | 1 | 0 | 0 | 10 | ○ |
| Example 6 | 1.4 | 37 | 20 | 28 | 85 | 10.0 | 0 | 1 | 0 | 5 | ○ |
| Comparative Example 1 | 1.3 | 45 | 28 | 31 | 104 | 3.5 | 23 | 0 | 0 | 230 | Δ |
| Comparative Example 2 | 1.5 | 43 | 29 | 35 | 107 | 3.2 | 33 | 3 | 0 | 345 | ○ |
| Comparative Example 3 | 1.6 | 39 | 27 | 32 | 98 | 6.2 | 45 | 5 | 2 | 477 | ○ |
| Comparative Example 4 | 5.2 | 23 | 18 | 20 | 61 | 5.5 | 25 | x* | — | 250 (for ref.) | x |
| Comparative Example 5 | 3.4 | 47 | 35 | 42 | 124 | 38.4 | 49 | 34 | 30 | 690 | Δ | x* . . . The water-absorbent resin was spilled in a large amount upon supplying the liquid, thereby destroying the sheet.

It can be seen from Tables 1 and 2 that even with the same amount of the water-absorbent resin used, water-absorbent sheet compositions using water-permeable substrates in Examples 1 to 6 have excellent properties in permeation rates, amount of re-wet, and a leakage index at slope. Further, it can be seen that if a water-permeable substrate as defined in the present invention is used, the properties are even more enhanced.

EXAMPLE 7, COMPARATIVE EXAMPLE 6

Manufacture of Absorbent Articles

A back sheet side of a product manufactured by Procter and Gamble under the trade name Pampers Cottoncare (L size) was cut to open, and the contents were carefully removed so as not to destroy the top sheet. Each of the water-absorbent sheet compositions obtained in Example 2 and Comparative Example 2 cut into pieces of 10 cm×40 cm were inserted from the cut in a manner that a primary absorbent layer was located on the top sheet side, and sealed, to give absorbent articles (Example 7, Comparative Example 6). A test was conducted on 10 panelists using these absorbent articles. As a result, an evaluation was obtained that the absorbent article of Example 7 is more excellent in the aspect of feel, dry feel upon exchanging diapers, and liquid leakage.

It can be seen that the water-absorbent sheet compositions of Examples 1 to 6 and the absorbent article of Example 7 are water-absorbent sheet compositions and an absorbent article which accomplished thinning and avoidance of the gel blocking phenomenon even though the water-absorbent resin is contained in a large amount, while obtaining basic properties (strength, permeation rate, amount of re-wet, and amount of liquid leakage) at high levels.

INDUSTRIAL APPLICABILITY

The water-absorbent sheet composition of the present invention can be used for absorbent articles in hygienic material fields, agricultural fields, construction material fields, and the like, among which the water-absorbent sheet composition can be suitably used for absorbent articles in the hygienic material fields.

| EXPLANATION OF NUMERICAL SYMBOLS | |
|---|---|
| 1 | graduated cylinder |
| 2 | spacer |
| 3 | metallic tray |
| 4 | balance |
| 5 | water-permeable substrate |
| 6 | acrylic cylinder (supplying inlet) |
| 7 | glass filter |
| 8 | clamp |
| 11 | acrylic plate |
| 12 | acrylic plate |
| 13 | water-absorbent sheet composition |
| 21 | stand |
| 22 | acrylic plate |
| 23 | water-absorbent sheet composition |
| 24 | dropping funnel |
| 25 | balance |
| 26 | metallic tray |

-continued

| | EXPLANATION OF NUMERICAL SYMBOLS |
|---|---|
| 51 | water-absorbent sheet composition |
| 52 | water-absorbent resin |
| 53 | primary absorbent layer |
| 54 | water-absorbent resin |
| 55 | secondary absorbent layer |
| 56 | water-permeable substrate |
| 57 | hydrophilic nonwoven fabric |

The invention claimed is:

1. A water-absorbent sheet composition, comprising a structure in which an absorbent layer comprising a water-absorbent resin and an adhesive is sandwiched with two or more sheets of at least one hydrophilic nonwoven fabric,
wherein the water-absorbent sheet composition has a structure in which the absorbent layer is separated in divided parts of a primary absorbent layer and a secondary absorbent layer with a water-permeable substrate having a water permeability index of from 20 to 90, and
wherein the water-absorbent resin is comprised in the absorbent layer in an amount of from 100 to 1000 g/m².

2. The composition of claim 1, wherein the water-permeable substrate is at least one member selected from the group consisting of a sanitary paper, a cellulose-comprising synthetic fiber nonwoven fabric, a rayon-comprising synthetic fiber nonwoven fabric, and a hydrophilically treated synthetic fiber nonwoven fabric.

3. The composition of claim 2, wherein the hydrophilic nonwoven fabric comprises at least one member selected from the group consisting of a rayon fiber, a polyolefin fiber, and a polyester fiber.

4. The composition of claim 2, wherein the adhesive is at least one member selected from the group consisting of a polyolefin-comprising adhesive, a polyester-comprising adhesive, an ethylene-vinyl acetate copolymer adhesive, and a stryrenic elastomer adhesive.

5. The composition of claim 2 wherein the adhesive is comprised in an amount of from 0.05 to 2.0 times a content of the water-absorbent resin, on a mass basis.

6. The composition of claim 1, wherein the hydrophilic nonwoven fabric comprises at least one member selected from the group consisting of a rayon fiber, a polyolefin fiber, and a polyester fiber.

7. The composition of claim 6, wherein the adhesive is at least one member selected from the group consisting of a polyolefin-comprising adhesive, a polyester-comprising adhesive, an ethylene-vinyl acetate copolymer adhesive, and a stryrenic elastomer adhesive.

8. The composition of claim 1, wherein the adhesive is at least one member selected from the group consisting of a polyolefin-comprising adhesive, a polyester-comprising adhesive, an ethylene-vinyl acetate copolymer adhesive, and a stryrenic elastomer adhesive.

9. The composition of claim 1, wherein the adhesive is comprised in an amount of from 0.05 to 2.0 times a content of the water-absorbent resin, on a mass basis.

10. The composition of claim 1, wherein a mass of a water-absorbent resin in the primary absorbent layer and a mass of a water-absorbent resin in the secondary absorbent layer are in a ratio, primary absorbent layer/secondary absorbent layer, of from 95/5 to 55/45.

11. The composition of claim 1, having all of properties (A) to (C):

(A) a thickness of 5 mm or less,
(B) a total permeation rate of 100 seconds or less, and
(C) a leakage index of 200 or less.

12. An absorbent article, comprising the composition of claim 1, sandwiched between a liquid-permeable sheet and a liquid-impermeable sheet.

13. A water-absorbent sheet composition, comprising a structure in which an absorbent layer comprising a water-absorbent resin and an adhesive is sandwiched with two or more sheets of at least one hydrophilic nonwoven fabric,
wherein the water-absorbent sheet composition has a structure in which the absorbent layer is separated in divided parts of a primary absorbent layer and a secondary absorbent layer with a water-permeable substrate having water permeability index of from 20 to 90, and
wherein the water-absorbent resin is comprised in the absorbent layer in an amount of from 200 to 800 g/m².

14. The composition of claim 13, wherein the water-permeable substrate is at least one member selected from the group consisting of a sanitary paper, a cellulose-comprising synthetic fiber nonwoven fabric, a rayon-comprising synthetic fiber nonwoven fabric, and a hydrophilically treated synthetic fiber nonwoven fabric.

15. The composition of claim 13, wherein the hydrophilic nonwoven fabric comprises at least one member selected from the group consisting of a rayon fiber, a polyolefin fiber, and a polyester fiber.

16. The composition of claim 13, wherein the adhesive is at least one member selected from the group consisting of a polyolefin-comprising adhesive, a polyester-comprising adhesive, an ethylene-vinyl acetate copolymer adhesive, and a stryrenic elastomer adhesive.

17. The composition of claim 13, wherein the adhesive is comprised in an amount of from 0.05 to 2.0 times a content of the water-absorbent resin, on a mass basis.

18. The composition of claim 13, wherein a mass of a water-absorbent resin in the primary absorbent layer and a mass of a water-absorbent resin in the secondary absorbent layer are in a ratio, primary absorbent layer/secondary absorbent layer, of from 95/5 to 55/45.

19. The composition of claim 13, having all of properties (A) to (C):

(A) a thickness of 5 mm or less,
(B) a total permeation rate of 100 seconds or less, and
(C) a leakage index of 200 or less.

20. An absorbent article, comprising the composition of claim 13, sandwiched between a liquid-permeable sheet and a liquid-impermeable sheet.

21. A water-absorbent sheet composition, comprising a structure in which an absorbent layer comprising a water-absorbent resin and an adhesive is sandwiched with two or more sheets of at least one hydrophilic nonwoven fabric,
wherein the water-absorbent sheet composition has a structure in which the absorbent layer is separated in divided parts of a primary absorbent layer and a secondary absorbent layer with a water-permeable substrate having a water permeability index of from 20 to 90, such that the primary absorbent layer and the secondary absorbent layer are in direct contact with the water-permeable substrate, and
wherein the water-absorbent resin is comprised in the absorbent layer in an amount of from 100 to 1000 g/m².

* * * * *